US010441754B2

(12) United States Patent
Richardson

(10) Patent No.: US 10,441,754 B2
(45) Date of Patent: Oct. 15, 2019

(54) INTRAVASCULAR DEVICES, SYSTEMS, AND METHODS HAVING A CORE WIRE FORMED OF MULTIPLE MATERIALS

(71) Applicant: Volcano Corporation, San Diego, CA (US)

(72) Inventor: Mark Richardson, Escondido, CA (US)

(73) Assignee: VOLCANO CORPORATION, San Diego, CA (US)

(*) Notice: Subject to any disclaimer, the term of this patent is extended or adjusted under 35 U.S.C. 154(b) by 169 days.

(21) Appl. No.: 14/663,185

(22) Filed: Mar. 19, 2015

(65) Prior Publication Data

US 2015/0273187 A1  Oct. 1, 2015

Related U.S. Application Data

(60) Provisional application No. 61/970,777, filed on Mar. 26, 2014.

(51) Int. Cl.

| A61M 25/09 | (2006.01) |
| A61B 5/0205 | (2006.01) |
| A61L 31/02 | (2006.01) |
| A61B 5/026 | (2006.01) |

(Continued)

(52) U.S. Cl.
CPC ............ *A61M 25/09* (2013.01); *A61B 5/026* (2013.01); *A61B 5/0215* (2013.01); *A61L 31/022* (2013.01); *A61L 31/10* (2013.01); *A61B 5/02055* (2013.01); *A61M 2025/09075* (2013.01); *A61M 2025/09108* (2013.01); *A61M 2025/09141* (2013.01); *A61M 2210/12* (2013.01); *A61M 2230/30* (2013.01);

(Continued)

(58) Field of Classification Search
CPC ... A61B 5/0245; A61B 5/7221; A61B 5/0452; A61B 5/7264; A61B 5/7203
See application file for complete search history.

(56) References Cited

U.S. PATENT DOCUMENTS

| 5,125,137 A | 6/1992 | Corl et al. |
| 5,873,835 A | 2/1999 | Hastings et al. |
| 6,039,699 A | 3/2000 | Viera |

(Continued)

FOREIGN PATENT DOCUMENTS

| EP | 1849409 A1 | 10/2007 |
| WO | 2014036507 A1 | 3/2014 |

OTHER PUBLICATIONS

Korean Intellectual Property Office, International Search Report and Written Opinion of the International Searching Authority for PCT/US2015/022020, dated Jun. 29, 2015, 11 pages.

*Primary Examiner* — Mark Bockelman

(57) ABSTRACT

Intravascular devices, systems, and methods are disclosed. In some instances, the intravascular device is a guide wire having a core wire formed of multiple materials. For example, a sensing guide wire is provided that includes a core member having an inner section and an outer section surrounding the inner section, wherein the inner section is formed of a first material and the outer section is formed of a second material that is different than the first material; and a sensing element coupled to a distal portion of the core member. Methods of making, manufacturing, and/or assembling such intravascular devices and associated systems are also provided.

21 Claims, 6 Drawing Sheets

(51) Int. Cl.
*A61B 5/0215* (2006.01)
*A61L 31/10* (2006.01)

(52) U.S. Cl.
CPC .... *A61M 2230/50* (2013.01); *Y10T 29/49169* (2015.01); *Y10T 29/49171* (2015.01)

(56) References Cited

U.S. PATENT DOCUMENTS

| | | | |
|---|---|---|---|
| 6,106,476 | A | 8/2000 | Corl et al. |
| 6,329,069 | B1 * | 12/2001 | Azizi ................ B21C 37/042 428/600 |
| 6,551,250 | B2 | 4/2003 | Khalil |
| 7,930,014 | B2 | 4/2011 | Huennekens et al. |
| 2003/0028128 | A1 | 2/2003 | Tenerz |
| 2003/0216668 | A1 | 11/2003 | Howland et al. |
| 2004/0039434 | A1 * | 2/2004 | Schrom ................ A61N 1/0551 607/118 |
| 2007/0255145 | A1 | 11/2007 | Smith |
| 2009/0118705 | A1 | 5/2009 | Chen |
| 2010/0004562 | A1 | 1/2010 | Jalisi et al. |
| 2010/0274619 | A1 | 10/2010 | Maresh et al. |
| 2014/0005543 | A1 | 1/2014 | Burkett |
| 2014/0005560 | A1 | 1/2014 | Burkett |
| 2014/0180141 | A1 | 6/2014 | Millett |
| 2014/0187874 | A1 | 7/2014 | Burkett et al. |
| 2014/0187980 | A1 | 7/2014 | Burkett |
| 2014/0187984 | A1 | 7/2014 | Burkett |

* cited by examiner

INTRAVASCULAR DEVICES, SYSTEMS, AND METHODS HAVING A CORE WIRE FORMED OF MULTIPLE MATERIALS

CROSS REFERENCE TO RELATED APPLICATIONS

The present application claims priority to and the benefit of the U.S. Provisional Patent Application Nos. 61/970,777, filed Mar. 26, 2014 which is hereby incorporated by reference in their entirety.

TECHNICAL FIELD

The present disclosure relates to intravascular devices, systems, and methods. In some embodiments, the intravascular devices are sensing guide wires that include a core wire formed of multiple materials.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. For example, the handling performance of previous guide wires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guide wire. Further, due to its small diameter, in many instances the proximal connector portion of the guide wire (i.e., the connector(s) that facilitate communication between the electronic component(s) of the guide wire and an associated controller or processor) is fragile and prone to kinking, which can destroy the functionality of the guide wire. For this reason, surgeons are reluctant to remove the proximal connector from the guide wire during a procedure for fear of breaking the guide wire when reattaching the proximal connector. Having the guide wire coupled to the proximal connector further limits the maneuverability and handling of the guide wire.

Further, a problem with existing pressure and flow guide wires is that they require a complex assembly of many discrete components. That complex assembly process has limitations on design performance of the guide wire. The use of separate conductive wires running down the length of the wire reduces the space available for more supportive cores and can result in numerous issues during use due to poor solder joints with conductive bands, electrical shorts due to insulation issues, and breakage of the delicate conductive wires.

Accordingly, there remains a need for improved intravascular devices, systems, and methods that include one or more electronic, optical, or electro-optical components.

SUMMARY

The present disclosure is directed to intravascular devices, systems, and methods that include a guide wire having a core wire formed of multiple materials.

The present disclosure provides a more robust sensing guide wire that avoids the assembly and performance issues of prior sensing guide wires. Guide wires of the present disclosure have a core wire formed of multiple materials. For example, in some implementations the core wire is formed of two different metals co-drawn to form the core wire. The core wire is covered by an outer layer embedded with electrical conductors. The electrical conductors extend along the length of the guide wire and act as the electrical pathway for sensor signals. The electrical conductors can be electrically isolated from the core wire by an insulating material of the outer layer. The electrical conductors can be exposed by removing surrounding portions of the outer layer (e.g., by ablating, cutting, etching, etc.) at specific locations to facilitate the creation of electrical connections. In that regard, a proximal section of each conductor can be electrically coupled to a proximal connector (e.g., one or more conductive bands), while a distal section of the conductor can be electrically coupled to a sensing element. In that regard, the distal section of the conductor may be exposed for electrical connection as part of a distal shaping process. In some instances, the distal shaping process includes removing one of the materials of the core wire. For example, where two metals are co-drawn such that one metal surrounds the other metal, portions of the outer metal layer and/or the inner metal layer can be removed (e.g., by grinding, etching, ablating, etc.) to define a desired structure for a distal section of the core.

Any type of sensor can be connected to guide wires of the present disclosure. In certain embodiments, only a single sensor is connected to the guide wire. In other embodiments, multiple sensors are connected to the guide wire. All of the sensors may be the same. Alternatively, the sensors may differ from each other and measure different characteristics inside a vessel. Exemplary sensors are pressure, flow, and temperature sensors. Generally, any type of pressure sensor may be used with the guide wires of the present disclosure, including piezoresistive, optical, and/or combinations thereof. Similarly, any type of flow sensor may be used with guide wires of the present disclosure. In certain embodiments, the flow sensor includes an ultrasound transducer, such as a Doppler ultrasound transducer. The guide wires can include both a pressure sensor and a flow sensor.

The present disclosure provides intravascular devices that are stronger and more durable than existing designs, while also easier to manufacture. For example the guide wires of the present disclosure can eliminate the need for a hypotube and substantially reduce the need for adhesives and solder in formation of the guide wire. Reducing the number of components necessary to assemble the guide wires improves the robustness of the assembled guide wire by eliminating a multitude of processes and connection points that can create failure conditions. Embodiments of the present disclosure utilize a core member formed of two different materials and surrounded by an outer layer embedded with one or more electrical conductors that facilitates the use of a larger core that provides better handling, strength, and durability than existing designs, which reduces the likelihood of unwanted bending, kinking, and/or other damage to the intravascular device that can be detrimental to the function of the device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
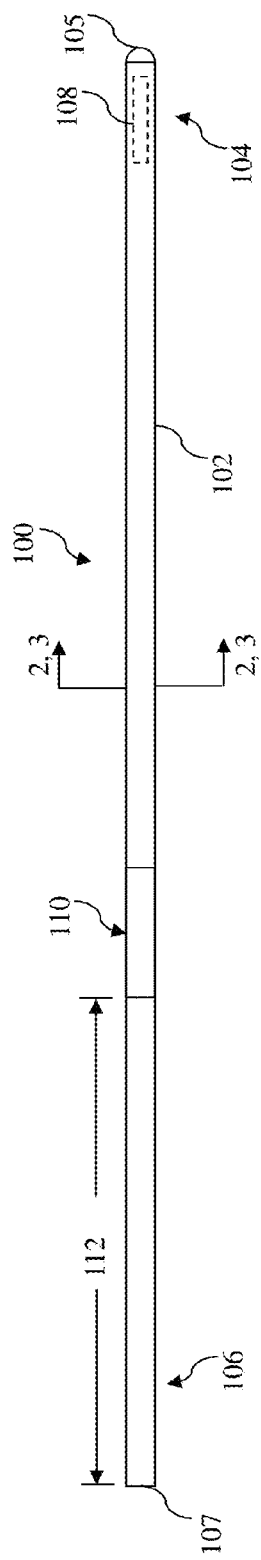
FIG. 1 is a diagrammatic, schematic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal end 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a flow sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Further, in some embodiments the connector 110 provides both electrical and optical connections to both electrical conductor(s) and optical communication pathway(s) coupled to the component 108. In that regard, it should be noted that component 108 is comprised of a plurality of elements in some instances. The connector 110 is configured to provide a physical connection to another device, either directly or indirectly. In some instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. Generally, any number of electrical conductors, optical pathways, and/or combinations thereof can extend along the length of the core of the flexible elongate member 102 between the connector 110 and the component 108. In some instances, between one and ten electrical conductors and/or optical pathways extend along the length of the flexible elongate member 102 between the connector 110 and the component 108. The number of communication pathways and the number of electrical conductors and optical pathways extending along the length the flexible elongate member 102 is determined by the desired functionality of the component 108 and the corresponding elements that define component 108 to provide such functionality.

Referring now to FIGS. 2-6, shown therein are aspects of the intravascular devices of the present disclosure that include a core member formed of multiple materials. In that regard, one of the major issues associated with existing functional guide wires is poor mechanical performance as compared to frontline guide wires. This performance loss is due in a large part to the typical design of the guide wires that severely limits the space available for the core or core wire due to the need to run the communication lines along the length of the device between the core wire and a surrounding hypotube. For the sake of clarity and simplicity, the embodiments described below include either three or six electrical conductors embedded in an outer layer surrounding a core member formed of multiple materials, which may include conductive materials suitable for use as a communication line. Those skilled in the art will recognize that the concepts are applicable to intravascular devices that include virtually any number of electrical conductors and/or optical fibers extending along the length of the core wire. However, in most implementations the intravascular device will include between 1 and 10 communication pathways extending between a proximal portion and a distal portion of the intravascular device.

Figure 2:
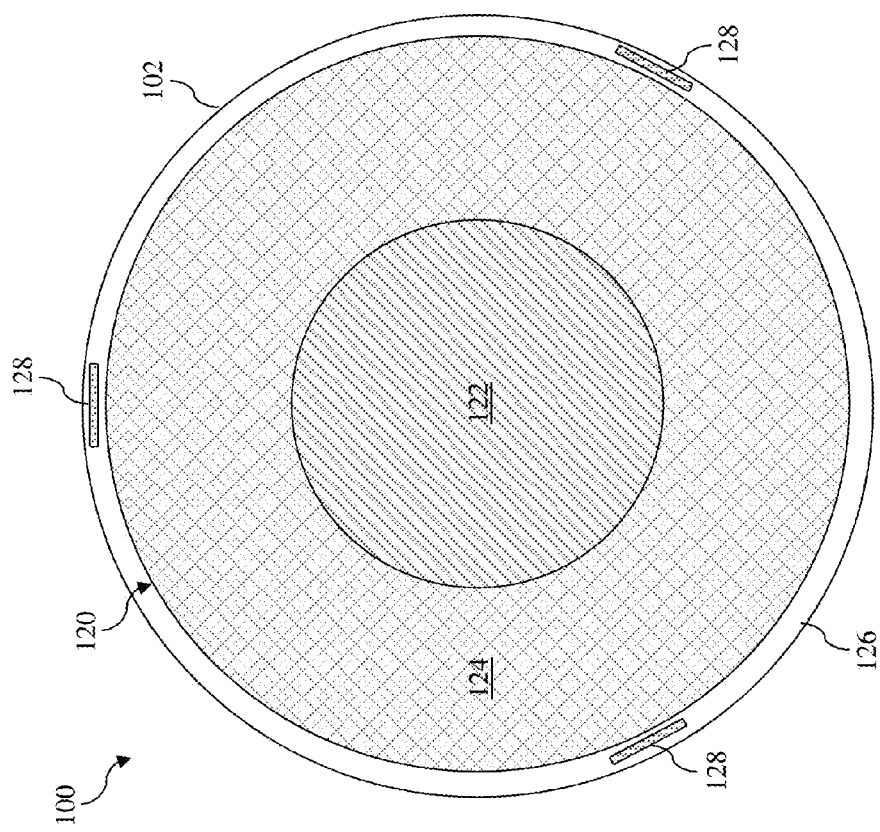
FIG. 2 is a cross-sectional end view of the intravascular device of FIG. 1 according to an embodiment of the present disclosure.

Referring more specifically to FIG. 2, a cross-sectional end view of the intravascular device 100 taken along section line 2-2 of FIG. 1 is shown according to an embodiment of the present disclosure. As shown, the flexible elongate member 102 is defined by a core member 120. The core member 120 is defined by an inner section 122 and an outer section 124 that surrounds the inner section. The inner section 122 is formed of a first material and the outer section 124 is formed of a second material that is different than the first material. Generally, the inner section 122 and the outer section 124 can be formed from any suitable materials, including without limitation stainless steel, nickel and titanium alloys (such as Nitinol), polyetheretherketone, 304V stainless steel, MP35N, L605, and/or other suitable metallic or polymeric materials.

In some implementations, the inner section 122 and the outer section 124 are formed of two different metals that are co-drawn together to form the core member 120. In some particular instances, the inner section 122 is formed from a superelastic metal, such as Nitinol, Nitinol alloys, NiTiCo, and other suitable materials, that may have a high yield strength to improve durability of the working distal portion of the intravascular device 100. In some instances, the outer section 124 is formed from a metal having a higher modulus than that of the inner section 122, such as stainless steel, MP35N, L605, or other suitable metal, to improve the stiffness of the overall intravascular device 100 for better push strength and/or column strength. In other instances, the outer section 124 is formed of from a superelastic metal, such as Nitinol, Nitinol alloys, NiTiCo, and other suitable materials, and the inner section 122 is formed from a metal having a higher modulus, such as stainless steel, MP35N, L605, or other suitable metal.

An outer layer 126 is formed around the core member 120 in some instances. The outer layer 126 can be formed of a suitable polymeric material. In that regard, the outer layer 126 is coated onto the wire using standard wire coating techniques in some instances. As the thickness of the coating is built up, conductors 128 are introduced into the coating process such that they become completely coated in the polymeric material. The outer layer 126 may be formed of any suitable polymeric material, and a preferred material is polyimide. Each of the conductors 128 is formed of a conductive material, such as copper, gold, silver, platinum, or other suitable conductive material. Generally, the size of the conductors 128 is selected to allow the conductors 128 to be fully embedded within the material forming the outer layer 126. In certain embodiments, the conductors 128 are space substantially equally around a circumference of the flexible elongate member 102. However, the conductors 128 may be embedded in any suitable manner and/or pattern, including symmetric, non-symmetric, geometric, and non-geometric patterns.

In certain embodiments, after reaching a desired outer diameter, a final coating that can provide lubricity is applied to the outer surface of the outer layer 126. In some embodiments, the coating extends along a majority of the length of the flexible elongate member between the proximal portion 106 and the distal portion 104. The coating can be a suitable hydrophilic or hydrophobic coating. In some implementations, the coating provides increased lubricity. Exemplary coating materials include, without limitation, PTFE impregnated polyimide, silicone-based coatings, and hydrophilic based coatings. Generally, the coating will be a very thin layer of material. For example, in some implementations the coating has a thickness less than about 0.0010", less than about 0.0001", and/or less than about 0.00005". In some arrangements, a lubricious coating is blended with or mixed into the outer layer 126 to create a lubricious layer without a definitie break between materials.

The outer layer 126 can be utilized to electrically isolate the conductors 128 from each other and the core member 120. As a result, each of the conductors 128 and/or the core member 120 can be utilized as an independent electrical communication pathway of the intravascular device 100. In some instances, the conductors 128 are coated with an insulating material prior to being embedded within the outer layer 126. That is, an insulated conductor is provided separately and then embedded within the outer layer 126 during formation of the core member. In other instances, the outer layer 126 and conductors 128 are formed as part of an integrated process.

The outer diameter of the core member 120 is sized to allow for formation of one or more outer layers, such as outer layer 126, around the core member 120. Accordingly, where the intravascular device 100 is intended to have an outer diameter of approximately 0.014", the outer diameter of the core member 120 can be between about 0.006" and about 0.0135", between about 0.008" and about 0.013", or between about 0.009" and about 0.012". Further, the inner section 122 and the outer section 124 can be formed in any ratio of sizes to define the overall diameter of the core member 120. That is, the inner section 122 can be larger, by volume or cross-sectional area, than the outer section 124, or vice versa. Accordingly, in some instances the inner section 122 of the core member has an outer diameter between about 0.001" and about 0.012", while the outer section of the core member has a thickness (from its inner surface adjacent the inner section 122 to its outer surface adjacent the outer layer 126) between about 0.001" and about 0.0065". The relative sizes of the inner section 122 and the outer section 124 can be selected based on the materials used for each section. It is understood that the relative sizes of the inner section 122 and the outer section 124 may be dependent upon the desired outer diameter of the intravascular device 100, which as discussed above may include sizes of approximately 0.014", 0.018", 0.035", 0.038" and/or other suitable sizes.

Figure 3:
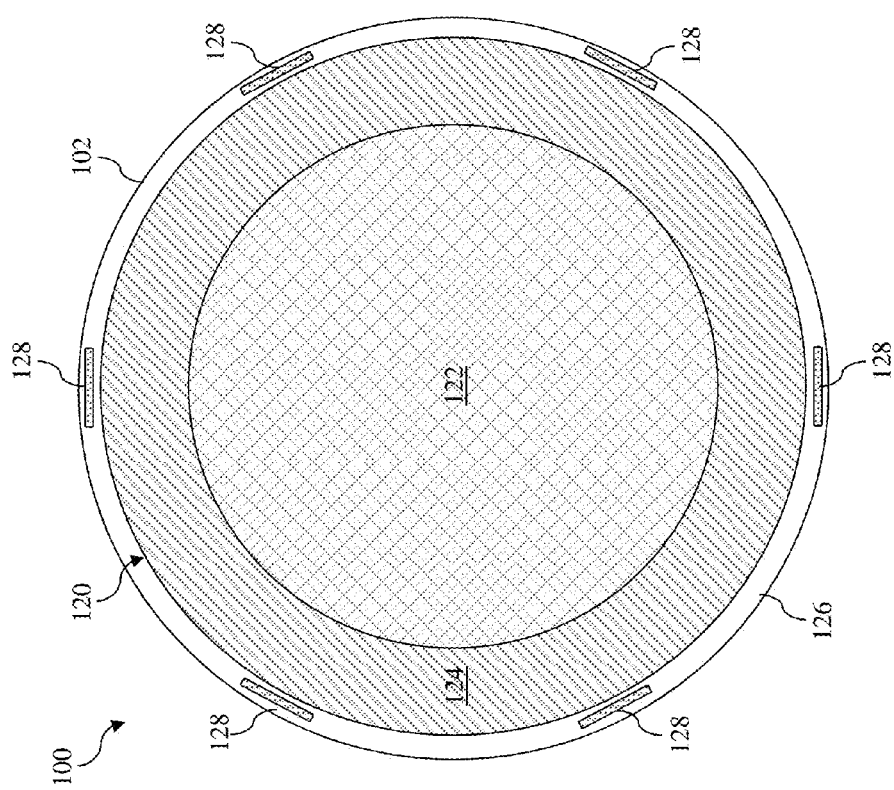
FIG. 3 is a cross-sectional end view of the intravascular device of FIG. 1 according to another embodiment of the present disclosure.

Referring now to FIG. 3, a cross-sectional end view of the intravascular device 100 taken along section line 3-3 of FIG. 1 is shown according to another embodiment of the present disclosure. In that regard, FIG. 3 shows an alternative embodiment to that of FIG. 2. In particular, FIG. 3 illustrates an embodiment where the inner section 122 of the core member 120 has an increased diameter such that the outer section 124 defines a smaller percentage of the core member 120. Further, FIG. 3 illustrates an embodiment with six conductors 128 embedded within the outer layer 126. Further still, FIG. 3 illustrates an embodiment where the material used to form the inner and outer sections 122, 124 has been reversed relative to the embodiment of FIG. 2. It is understood that FIG. 3 shows merely one exemplary alternative embodiment and that the intravascular devices of the present disclosure can use any variation of core materials, core diameter sizes, ratios of core materials, number of conductors, arrangement of conductors, and/or other variations in the design.

Figure 4:
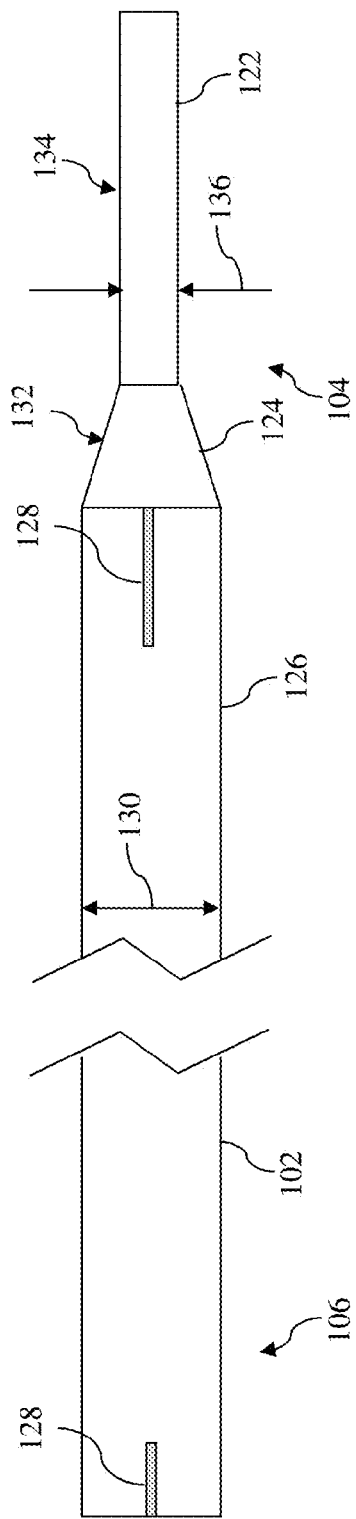
FIG. 4 is a diagrammatic, schematic side view of portions of an intravascular device according to an embodiment of the present disclosure.

Referring now to FIG. 4, shown therein is diagrammatic side view of the flexible elongate member 102 according to an embodiment of the present disclosure. In that regard, the flexible elongate member 102 is shown with the distal portion 104 and proximal portion 106 having been processed for use in the intravascular device 100. In particular, the distal portion 104 has been processed to expose a portion of the conductors 128 for electrical coupling to component 108 and shape the inner core member 120 to facilitate coupling to one or more flexible members and/or a sensor housing, facilitate physical coupling to the component 108, increase the flexibility of the distal tip of the intravascular device 102, and/or otherwise configure the characteristics of the distal portion of the intravascular device 102 for use.

As shown the main body of the flexible elongate member 102 has a diameter 130. Generally, the diameter 130 is approximately equal to the maximum desired outer diameter of the intravascular device 100. Accordingly, in some particular implementations the diameter 130 is about 0.014", 0.018", or 0.035". As shown, the distal portion 104 of the flexible elongate member 102 has been processed to include a portion 132 extending distally from the main body of the flexible elongate member 102 and a portion 134 extended distally from portion 132. In some instances, the distal portion 104 is processed by grinding, etching, ablating, and/or otherwise removing portions of the outer layer 126 and/or the core member 120.

As shown, portions of the outer layer 126 have been removed to expose sections of the embedded conductors 128. By exposing the conductors 128, the component 108 can be electrically coupled to the conductors 128 (e.g., using solder, leads, additional conductors (insulated in some instances)). In some implementations, the conductors 128 are exposed for electrical coupling to component 108 at an end surface extending perpendicular to the longitudinal axis of the flexible elongate member 102. That is, the conductors 128 are not exposed along the length of the flexible elongate member 102 (as shown in FIG. 4), but rather are exposed at an end surface of the flexible elongate member (similar to what is shown in FIGS. 2 and 3), which may occur at an intermediate transition point(s), such as the end of main body or end of section 132 and/or an end of the outer layer 126.

In the illustrated embodiment, section 132 has a tapered profile resulting from removal of the outer layer 126 and at least portions of the outer section 124 and/or the inner section 122 of the core member 120. In this manner, section 132 tapers the outer profile of the core member 120 from the diameter 130 of the main body of the flexible elongate member 102 to the reduced diameter 136 of section 134. In some embodiments, in section 134 the outer layer 126 and the outer section 124 of the core member 120 are removed to reduce the stiffness and increase the flexibility of the flexible elongate member 102. Accordingly, in some instances, the diameter 136 of section 134 is between about 10% and about 80% of the diameter 130, with some particular embodiments being between about 30% and about 60% of the diameter 130. Accordingly, in some implementations, the diameter 136 of section 134 is between about 0.001" and about 0.005" for a 0.014" outer diameter intravascular device, with 0.002" being utilized in some particular embodiments; between about 0.001" and about 0.008" for a 0.018" outer diameter intravascular device, with 0.003" being utilized in some particular embodiments; and between about 0.0025" and about 0.010" for a 0.035" outer diameter intravascular device, with 0.007" being utilized in some particular embodiments.

In some instances, section 132 and/or section 134 are shaped in a manner to facilitate coupling to additional elements of the intravascular device 100, including component 108, a housing for component 108, flexible members (coils, polymer tubes, and/or coil-embedded polymer tubes), and/or combinations thereof. In that regard, the sections 132 and 134 can include tapers, recesses, projections, and/or other structural features to facilitate coupling to other elements. In some particular instances, the core member 120 is coupled to a distal section, intermediate section, and/or proximal section similar to those described in one or more of U.S. Pat. No. 5,125,137, U.S. Pat. No. 5,873,835, U.S. Pat. No. 6,106,476, U.S. Pat. No. 6,551,250, and U.S. patent application Ser. No. 13/931,052, filed Jun. 28, 2013, U.S. patent application Ser. No. 14/143,304, filed Dec. 30, 2013, each of which is hereby incorporated by reference in its entirety. In that regard, the component 108 can be mounted within a distal section of the intravascular device 100 using any suitable technique, including without limitation those disclosed in one or more of U.S. Pat. No. 5,125,137, U.S. Pat. No. 5,873,835, U.S. Pat. No. 6,106,476, U.S. Pat. No. 6,551,250, U.S. patent application Ser. No. 13/931,052, filed Jun. 28, 2013, U.S. patent application Ser. No. 14/135,117, filed Dec. 19, 2013, U.S. patent application Ser. No. 14/137,364, filed Dec. 20, 2013, and U.S. patent application Ser. No. 14/139,543, filed Dec. 23, 2013, and U.S. patent application Ser. No. 14/143,304, filed Dec. 30, 2013, each of which is hereby incorporated by reference in its entirety.

As shown, the proximal portion 106 of the core member 120 has been processed to expose the embedded conductors 128. By exposing the conductors 128, one or more connectors can be electrically coupled to the conductors 128 (e.g., using solder, leads, additional conductors (insulated in some instances) to define connector 110 of the intravascular device 100.

Figure 5:
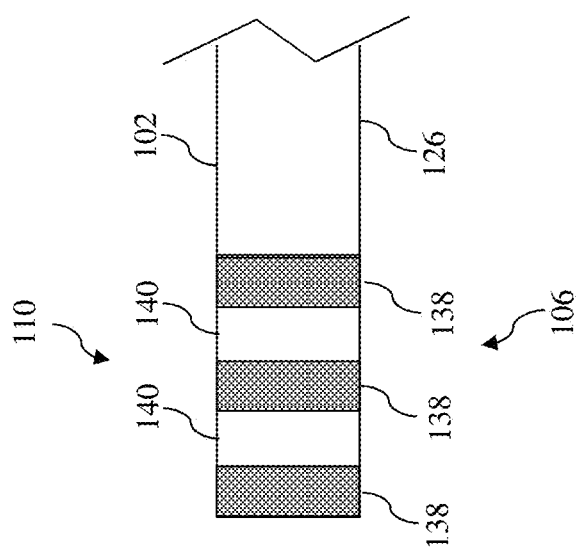
FIG. 5 is a diagrammatic, schematic side view of a proximal portion of an intravascular device according to an embodiment of the present disclosure.

Referring now to FIG. 5, shown therein is the proximal portion 106 of the intravascular device 100 formed over the flexible elongate member 102 of FIG. 4 according to an embodiment of the present disclosure. As shown, three conductive bands 138 are separated by insulators 140 to define the connector 110 of the intravascular device 100. In some instances, the conductive bands 138 are printed onto the flexible elongate member 102 by electrically printing or plating of a conductive material over the exposed portions of the conductors 128. In that regard, the conductive bands 138 are formed such that they have a uniform outer diameter matching the desired outer diameter of the intravascular device 100 and/or the outer diameter of connector in some implementations. To facilitate formation of each of the conductive bands 128 in an electrically isolated manner relative to the other conductors 128, the embedded conductors 128 are exposed and then coated with an insulator material, such as polyimide. Then each individual conductor 128 is exposed (e.g., via laser ablation) at staggered locations along the length of the flexible elongate member 102 that represent where the conductive bands 138 will be formed. In this manner, each conductive band 138 is electrically coupled to a single conductor 128 and electrically isolated from the remaining conductors 128. If desired, it is possible to electrically couple a conductive band 138 to more than one of the conductors 128.

Any desired pattern of conductive material may be placed onto the flexible elongate member 102 to define the conductive bands 138. For example, the conductive bands 138 can be solid, multiple rings, a spiral, and/or any other pattern that provides the optimum functionality. In some instances, the conductive bands 138 are preformed cylindrical members that are positioned over the corresponding exposed sections of the conductors 128 and electrically coupled to the conductors using solder or other suitable techniques. In some embodiments, the conductive bands 138 are swaged and/or laser welded in place. The insulating material utilized for insulators 140 may be any suitable insulating material.

In the illustrated embodiment, each of the three conductive bands 138 is electrically coupled to a single one of the conductors 128 and electrically isolated from the others (e.g., by one or more insulating layers). In some instances, the conductors 128 are exposed from the outer layer 126 only in locations along the length of the core member where the conductor 128 is to be coupled to the conductive band. A reference ring may be formed at a proximal or distal end of the flexible elongate member 102 to determine where the conductors 128 are positioned relative to the circumference/outer surface of the flexible elongate member 102 to facilitate selective exposure of only portions of the conductors 128. Those skilled in the art will recognize that there are numerous ways for electrically coupling the conductive bands 138 to the conductors 128 in an isolated manner. Further, it should be noted that in some instances an additional conductive band is provided and electrically coupled to the core member 120. In yet other instances, a portion of the core member 120 itself defines a conductive band.

Figure 6:
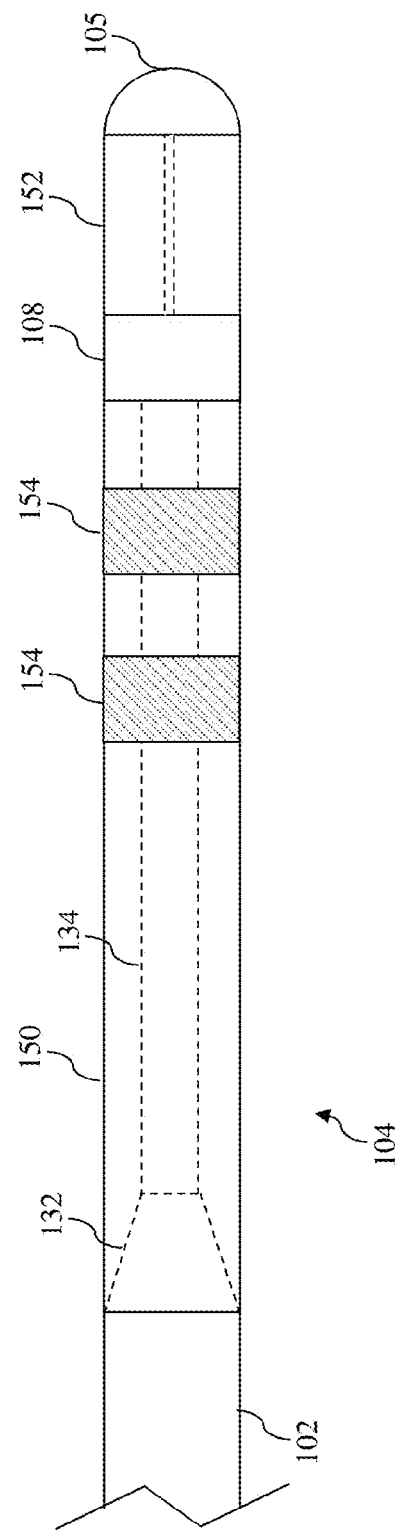
FIG. 6 is a diagrammatic, schematic side view of a distal portion of an intravascular device according to an embodiment of the present disclosure.

Referring now to FIG. 6, shown therein is the distal portion 104 of the intravascular device 100 formed over the core member 120 of FIG. 4 according to an embodiment of the present disclosure. As shown, the distal portion 104 includes a flexible element 150 extending from the main body of the flexible elongate member 102 over sections 132 and 134 to the component 108 (or a housing containing component 108). In that regard, the flexible element 150 may be a coil, a polymer tubing, and/or a coil-embedded polymer tubing. The distal portion 104 also includes a flexible element 152 extending distally from the component 108 (or a housing containing component 108) to the distal tip 105 of the intravascular device 100. Again, the flexible element 152 may be a coil, a polymer tubing, and/or a coil-embedded polymer tubing. In some instances, the flexible element 152 is radiopaque and/or includes a radiopaque tip. In some implementations, a flow sensor is positioned at the distal tip 105 of the intravascular device 100. Generally, the distal portion 104 of the intravascular device 100 may include features similar to those described in any of the patents and applications incorporated by reference above, but utilizing the core member 120 of the present disclosure having embedded conductors 124 as the core wire of the intravascular device.

As also shown in FIG. 6, the distal portion 104 can include one or more radiopaque markers 154. In that regard, the radiopaque markers 154 can be utilized to facilitate co-registration of the measurements obtained with the intravascular device 100 to corresponding images of the vessel, including angiography, x-ray, CT scans, IVUS, OCT, and/or other imaging modalities. In some implementations, co-registration is performed as disclosed in one or more of U.S. Pat. No. 7,930,014, titled "VASCULAR IMAGE CO-REGISTRATION," U.S. Provisional Patent Application No. 61/747,480, titled "SPATIAL CORRELATION OF INTRAVASCULAR IMAGES AND PHYSIOLOGICAL FEATURES" and filed Dec. 31, 2012, U.S. Provisional Patent Application No. 61/856,509, titled "DEVICES, SYSTEMS, AND METHODS FOR ASSESSMENT OF VESSELS" and filed Jul. 19, 2013, and U.S. Provisional Patent Application No. 61/895,909, titled "DEVICES, SYSTEMS, AND METHODS FOR VESSEL ASSESSMENT" and filed Oct. 25, 2013, each of which is hereby incorporated by reference in its entirety.

The radiopaque markers 154 can be formed of any radiopaque material. In some instances, the radiopaque markers 154 are coils formed of a radiopaque material. There may be any number of radiopaque markers 154, including one, two (as shown), three, or more. In some implementations, the radiopaque markers 154 are located proximal of the component 108 and its associated housing, if any. Further, in some instances the radiopaque markers 154 are elongated such that they have a greater length than typical balloon or stent markers, to allow the radiopaque markers 154 of the intravascular device 100 to be distinguished from the markers of other elements that may be positioned in the same region of the vessel. In some instances, the radiopaque markers 154 have a length along the longitudinal axis of the intravascular device 100 of between about 3 mm and about 10 mm, with some particular implementations having a length of about 5 mm.

As discussed above with respect to component 108, the sensor(s) of the intravascular device 100 provide a mechanism to obtain intraluminal measurements within a body lumen and are connected to the one or more conductive bands on the intravascular device, which transmit and receive signals from the sensor(s). For example, the guide wire of the present disclosure can include a pressure sensor, a flow sensor, a temperature sensor or combinations thereof. The guide wire can be a combination guide wire that includes both a pressure sensor and a flow sensor. Pressure sensors can be used to measure pressure within the lumen and flow sensors can be used to measure the velocity of blood flow. Temperature sensors can measure the temperature of a lumen. A guide wire with both a pressure sensor and a flow sensor provides a desirable environment in which to calculate fractional flow reserve (FFR) or other pressure ratio calculations using pressure readings, and coronary flow reserve (CFR) using flow readings. Guide wires with two or more sensors can be made by increasing the number of conductive wires embedded within the core member. In addition, the core member 120 may also be utilized as a conductor in some embodiments. Such embodiments provide enough conductive pathways to facilitate the use of at least two sensors with the intravascular device 100.

The ability to measure and compare both the pressure and velocity flow and create an index of hyperemic steno sis resistance significantly improves the diagnostic accuracy of this ischemic testing. It has been shown that distal pressure and velocity measurements, particularly regarding the pressure drop-velocity relationship such as Fractional Flow reserve (FFR), Coronary flow reserve (CFR) and combined P-V curves, reveal information about the stenosis severity. For example, in use, the guide wire may be advanced to a location on the distal side of the stenosis. The pressure and flow velocity may then be measured at a first flow state. Then, the flow rate may be significantly increased, for example by the use of drugs such as adenosine, and the pressure and flow measured in this second, hyperemic, flow state. The pressure and flow relationships at these two flow states are then compared to assess the severity of the stenosis and provide improved guidance for any coronary interventions. The ability to take the pressure and flow measurements at the same location and same time with the combination tip sensor, improves the accuracy of these pressure-velocity loops and therefore improves the accuracy of the diagnostic information.

A pressure sensor can be mounted, for example, on a distal portion of the guide wire. The pressure sensor can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires of the sensor are connected to a conductive band in the guide wire. Additional details of suitable pressure sensors that may be used with devices of the present disclosure are described in U.S. Pat. No. 6,106,476. U.S. Pat. No. 6,106,476 also describes suitable methods for coupling the pressure sensor to a guide wire. Those methods are applicable to coupling the sensor to the conductive bands in guide wires of the present disclosure.

In certain aspects, the guide wire of the present disclosure includes a flow sensor. The flow sensor can be used to measure blood flow velocity within the vessel, which can be used to assess coronary flow reserve (CFR). The flow sensor can be, for example, an ultrasound transducer, a Doppler flow sensor or any other suitable flow sensor, disposed at or in close proximity to the distal tip of the guide wire. The ultrasound transducer may be any suitable transducer, and may be mounted in the distal end using any conventional method, including the manner described in U.S. Pat. Nos. 5,125,137, 6,551,250 and 5,873,835.

Guide wires of the present disclosure can be connected to an instrument, such as a computing device (e.g. a laptop, desktop, or tablet computer) or a physiology monitor, that converts the signals received by the sensors into pressure and velocity readings. The instrument can further calculate Coronary Flow Reserve (CFR) and Fractional Flow Reserve (FFR) and provide the readings and calculations to a user via a user interface. In some embodiments, a user interacts with a visual interface to view images associated with the data obtained by the intravascular devices of the present disclosure. Input from a user (e.g., parameters or a selection) are received by a processor in an electronic device. The selection can be rendered into a visible display.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A sensing guide wire, comprising:
a core member comprising an inner section and an outer section surrounding the inner section, wherein the inner section is formed of a first material and the outer section is formed of a second material that is different than the first material;
a single outer layer surrounding the core member;
a flexible element coupled to a distal portion of the core member;
a sensing element adjacent to the flexible element;
a connector coupled to a proximal portion of the sensing guide wire; and
at least one communication line embedded within the single outer layer such that the at least one communication line and the core member are isolated by the single outer layer,
wherein the single outer layer is directly in contact with both the core member and the at least one communication line,
wherein the sensing element is communicatively coupled to the connector via the at least one communication line, and
wherein the at least one communication line comprises an exposed section at a distal portion of the sensing guide wire, wherein the exposed section is exposed by removal of a portion of the single outer layer at the distal portion of the sensing guide wire, and wherein the sensing element is electrically coupled to the at least one communication line by an electrical coupling between the exposed section and the at least one communication line.

2. The guide wire of claim 1, wherein the sensing element includes at least one of a pressure sensor or a flow sensor.

3. The guide wire of claim 1, wherein the single outer layer comprises a polymer outer layer.

4. The guide wire of claim 1, wherein the at least one communication line includes at least one of a conductor or an optical fiber.

5. The guide wire of claim 1, wherein the first material is Nitinol or other nickel titanium alloy.

6. The guide wire of claim 5, wherein the second material is stainless steel or a high modulus alloy.

7. The guide wire of claim 1, wherein the first material is stainless steel.

8. The guide wire of claim 7, wherein the second material is Nitinol.

9. The guide wire of claim 1, wherein the guide wire has an outer diameter of between about 0.014" and about 0.038".

10. The guide wire of claim 9, wherein the inner section of the core member has an outer diameter between about 0.001" and about 0.012".

11. The guide wire of claim 10, wherein the outer section of the core member has a thickness between about 0.001" and about 0.0065".

12. The guide wire of claim 1, wherein at least the outer section is removed from a distal portion of the core member.

13. The guide wire of claim 12, wherein the sensing element is positioned within a housing coupled to the distal portion of the core member.

14. The guide wire of claim 13, wherein the flexible element is positioned around the distal portion of the core member proximal of the housing.

15. The guide wire of claim 13, wherein diameters of the inner section and the outer section are substantially equal.

16. The guide wire of claim 13, wherein a diameter of the inner section is larger than a diameter of the outer section.

17. The guide wire of claim 1, wherein the at least one communication line comprises a plurality of communication lines, and wherein the plurality of communication lines are spaced substantially equally around a circumference of the guide wire.

18. The guide wire of claim 1, wherein a portion of the single outer layer is directly in contact with an entire circumference of the core member and an entire circumference of the at least one communication line.

19. The guide wire of claim 1, wherein the first material and second material comprise metallic materials, and wherein the single outer layer is in direct contact with the second material of the outer section of the core member.

20. The guide wire of claim 1, wherein the at least one communication line comprises a proximal exposed section at the proximal portion of the sensing guide wire, wherein the proximal exposed section is exposed by removal of a portion of the single outer layer at the proximal portion of the sensing guide wire, and wherein the connector is communicatively coupled to the at least one communication line at the proximal exposed section.

21. The guide wire of claim 1, wherein the at least one communication line comprises a conductor, and wherein the connector comprises a conductive connector.

* * * * *